United States Patent
Sugiyama et al.

(10) Patent No.: US 6,903,236 B2
(45) Date of Patent: Jun. 7, 2005

(54) PROCESS FOR PRODUCING FLUOROCARBOXYLIC ANHYDRIDE

(75) Inventors: Akinari Sugiyama, Settsu (JP); Takashi Shibanuma, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 450 days.

(21) Appl. No.: 10/168,560

(22) PCT Filed: Dec. 12, 2000

(86) PCT No.: PCT/JP00/08765
§ 371 (c)(1),
(2), (4) Date: Jun. 21, 2002

(87) PCT Pub. No.: WO01/46113
PCT Pub. Date: Jun. 28, 2001

(65) Prior Publication Data
US 2002/0183550 A1 Dec. 5, 2002

(30) Foreign Application Priority Data
Dec. 21, 1999 (JP) .......... 113-62631

(51) Int. Cl.⁷ .......... C02C 51/56
(52) U.S. Cl. .......... 562/897
(58) Field of Search .......... 562/897

(56) References Cited

U.S. PATENT DOCUMENTS

| 3,676,491 A | 7/1972 | Wada et al. |
| 4,595,541 A | 6/1986 | Amiet et al. |

FOREIGN PATENT DOCUMENTS

| JP | 45-38523 B1 | 12/1970 |
| JP | 45 38523 | 12/1970 |
| JP | 46 6888 | 2/1971 |
| JP | 61 33139 | 2/1986 |

OTHER PUBLICATIONS

Bourne et al., J. Chem. Soc. (1949) 2976–2979.

*Primary Examiner*—Paul J. Killos
(74) *Attorney, Agent, or Firm*—Birch, Stewart, Kolasch & Birch, LLP

(57) ABSTRACT

A method of producing $(R_fCO)_2O$ by reacting $R_fCOCl$ with $M_mCO_3$ can efficiently synthesize a fluorocarboxylic anhydride in a one-step reaction,
wherein $R_f$ is a saturated hydrocarbon group having 1 to 20 carbon atoms, which optionally has an oxygen atom, in which all or part of hydrogen atoms are substituted with a fluorine atom, or a fluorine atom and another halogen atom, M is an alkali metal or an alkali earth metal, m is 2 when M is the alkali metal, or 1 when M is the alkali earth metal.

6 Claims, No Drawings

PROCESS FOR PRODUCING FLUOROCARBOXYLIC ANHYDRIDE

This application is the national phase under 35 U.S.C. § 371 of PCT International Application No. PCT/JP00/08765 which has an International filing date of Dec. 12, 2000, which designated the United States of America.

TECHNICAL FIELD

The present invention relates to a method of producing a fluorocarboxylic anhydride by using $R_fCOCl$ as a raw material.

RELATED ART

A method of synthesizing a fluorocarboxylic anhydride which is used as an agent for introducing $R_fCO$ and a dehydrating agent is known. For example, in the case of $(CF_3CO)_2O$, known are the following four synthesis procedures:

1. $CF_3CO_2H + P_2O_5 \rightarrow (CF_3CO)_2O +$ polyphosphoric acid (Bourne E. J., Stacey M., Tatlow J. C., Tedder J. M., J.Chem.Soc., 1949, 2976)
2. $(CHCl_2CO)_2O + 2CF_3CO_2H \rightarrow (CF_3CO)_2O + 2CHCl_2CO_2H$
   (JP-A-61-33139)
3. $CF_3COCl + ZnO, CuO, CdO \rightarrow (CF_3CO)_2O + ZnCl_2, CuCl_2, CdCl_2$
   (JP-B-46-6888)
4. $CF_3COCl + CF_3CO_2M \rightarrow (CF_3CO)_2O + MCl$ (M=Na, K, $Zn_{1/2}$, $Ba_{1/2}$)
   (JP-B-45-38523)

In Synthesis Procedure 1, $P_2O_5$ which is a hydrating agent can usually dehydrate three molecules of water, but $P_2O_5$ performs the ability of dehydrating only one molecule of water in the case of dehydrating perfluorocarboxylic acid. Therefore, a large amount of $P_2O_5$ is necessary and the reaction is quitted with having the remaining dehydrogenation ability. It is difficult to post-treating $P_2O_5$ after the reaction.

Synthesis Procedure 2 needs an excess amount of $CF_3CO_2H$, and $CF_3CO_2H$ has a small conversion ratio. In order to convert by-produced $CHCl_2CO_2H$ to an anhydride, a dehydrating agent (for example, $P_2O_5$) is additionally necessary and a waste treatment of the produced $H_3PO_4$ is also necessary.

Synthesis Procedure 3 needs an excess amount of $CF_3COCl$ and needs the cost for treatment of by-produced $ZnCl_2$ and the like.

Synthesis Procedure 4 has many steps, since a carboxylate salt, $CF_3CO_2M$ is provisionally reacted with $CF_3CO_2H$ and an alkali salt. In addition, $CF_3CO_2M$ has high deliquescence and it is difficult to control a water content.

SUMMARY OF INVENTION

An object of the present invention to provide a method of synthesizing $(R_fCO)_2O$ from $R_fCOCl$ without the above defects, for example, without using a plural of steps.

We intensively studied to solve the above problems and discovered that the use of $R_fCOCl$ and a low-cost carbonate salt of alkali metal or alkali earth metal can efficiently produce $(R_fCO)_2O$.

The present invention provides a method of producing $(R_fCO)_2O$ by reacting $R_fCOCl$ with $M_mCO_3$, wherein $R_f$ is a saturated hydrocarbon group having 1 to 20 carbon atoms, which optionally has an oxygen atom, in which all or part of hydrogen atoms are substituted with a fluorine atom, or a fluorine atom and another halogen atom, M is an alkali metal or an alkali earth metal, m is 2 when M is the alkali metal, or 1 when M is the alkali earth metal.

DETAILED EXPLANATION OF INVENTION

The method of preparing $(R_fCO)_2O$ by the reaction between $R_fCOCl$ and $M_mCO_3$ is represented by the reaction formula:

$$2R_fCOCl + M_mCO_3 \rightarrow (R_fCO)_2O + mMCl_{2/m} + CO_2$$

wherein $R_f$ is a saturated hydrocarbon group having 1 to 20 carbon atoms, which optionally has an oxygen atom, in which all or part of hydrogen atoms are substituted with a fluorine atom, or a fluorine atom and another halogen atom, M is an alkali metal or an alkali earth metal, m is 2 when M is the alkali metal, or 1 when M is the alkali earth metal.

$R_f$ is a saturated hydrocarbon group having 1 to 20 carbon atoms, particularly 1 to 10 carbon atoms, which optionally has an oxygen atom, in which all or part of hydrogen atoms are substituted with a fluorine atom, or a fluorine atom and another halogen atom. $R_f$ has at least one fluorine-containing atom.

$R_f$ may be:
$X(C_mX_{2m})_n$—,
$X(C_mX_{2m})_n(C_sX_{2s})_t$—
$X(C_mX_{2m}O)_n$—, or
$X(C_mX_{2m}O)_n(C_sX_{2s})_t$—
wherein each X is a halogen atom or a hydrogen atom, at least one X is a fluorine atom, n is an integer of 1 to 10, m is an integer of 1 to 5, s is an integer of 1 to 5, and t is an integer of 1 to 10.

$R_f$ may be a perfluoroalkyl group ($F(CF_2)_i$—), and may be liner or branched. i is from 1 to 20, for example, from 1 to 10, preferably from 1 to 7.

Specific examples of $R_fCOCl$ include:
$HCF_2COCl$
$CF_3COCl$
$CF_3CF_2COCl$
$CF_3CF_2CF_2COCl$
$H(CF_2CF_2)_nCOCl$
$Cl(CF_2CFCl)_nCF_2COCl$
$CF_3CF_2O(CF_2CF_2CF_2O)_nCF_2CF_2COCl$ and
$CF_3CF_2CF_2OCF(CF_3)COCl$
wherein n is from 1 to 10.

M is an alkali metal or an alkali earth metal, and is preferably Li, Na, K and/or Ca.

A yield of $(R_fCO)_2O$ is dependent on the used carbonate salt. The stabler a salt of $MCl_{2/m}$ produced at the reaction is, the higher the yield is. The carbonate salt is preferably $K_2CO_3$, $CaCO_3$, $Na_2CO_3$ and $Li_2CO_3$.

A molar ratio of $R_fCOCl$ to the carbonate salt is preferably at least 2.

A reaction temperature is preferably from 0° C. to 150° C., for example, from 10° C. to 50° C. If the reaction temperature is high, the product undesirably begins to decompose.

A reaction pressure is not specifically limited and may be from atmospheric pressure to 2 MPa (gauge pressure). When the reaction pressure is high, the raw material, $R_fCOCl$ is liquefied so that the contact between the reactants is improved so as to accelerate the reaction.

A reaction time is not specifically limited and may be from 20 minutes to 600 minutes, for example, from 120 minutes to 240 minutes.

In the present invention, $(R_fCO)_2O$ can be prepared in a one-step reaction with good yield by using $R_fCOCl$ and the low-cost carbonate salt of alkali metal or alkali earth metal.

A solvent may not be used in the present reaction. However, since the reaction is exothemic, the solvent may be used for the purpose of removing the heat.

A polar solvent and a nonpolar solvent can be used as the solvent.

Examples of the polar solvent include acetonitrile ($CH_3CN$), $CH_3O(CH_2CH_2O)_nCH_3$ (n=0~4), nitrobenzene ($C_6H_5NO_2$), dimethylformamide (DMF), dimethylsulfoxide (DMSO) and acetone.

Examples of the nonpolar solvent include a fluorine-containing solvent (for example, $C_4F_6Cl_4$ and $C_6F_9Cl_5$), $CCl_4$ and $C_nH_{2n+2}$ (n=5 to 10).

When the polar solvent is used, a carbonate gas is produced and then an anhydride is produced. When the nonpolar solvent is used, the carbonate gas may be produced simultaneously with production of the anhydride. The polar solvent may give easier treatment of the produced carbonate gas, and the easiness of the treatment is dependent on a reaction apparatus.

For example, when $R_fCOCl$ is $CF_3COCl$ and the carbonate salt is $Na_2CO_3$, a whole reaction is:

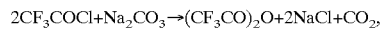
$$2CF_3COCl+Na_2CO_3 \rightarrow (CF_3CO)_2O+2NaCl+CO_2,$$

which whole reaction proceeds in two-step reactions:

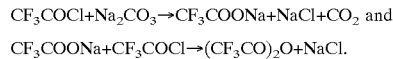
$$CF_3COCl+Na_2CO_3 \rightarrow CF_3COONa+NaCl+CO_2 \text{ and}$$
$$CF_3COONa+CF_3COCl \rightarrow (CF_3CO)_2O+NaCl.$$

The reaction can be proceeded in a one-step reaction, or the reaction can be divided into two steps as in the above. In this case, the drawing of the carbonate gas is advantageous in view point of an equipment (pressure resistance), since the pressure of the reactor does not become large. Particularly, when the polar solvent is used, the above two-step reaction can be quantatively proceeded. That is, when the $CF_3COCl$ raw material which is corresponding to the first step reaction (stoichemical amount of raw material) is introduced, the reaction stops after the first step reaction without the proceeding of the second step. When carbonate gas is released during the reaction, the release can be advantageously conducted without loss of the raw material. The second step reaction may be conducted at a temperature of at most 70° C., preferably at most 50° C., more preferably at most 30° C., since a reverse reaction of the second step reaction might proceed. Accordingly, these defined temperatures are preferable also when the object product is recovered. A distillation recovery is conducted preferably at a reduced pressure.

$(R_fCO)_2O$ obtained according to the present invention can be used as an agent for introducing $R_fCO$ and a dehydrating agent.

PREDERRED EMBODIMENTS OF INVENTION

Examples are shown hereinafter to illustrate the present invention.

EXAMPLE 1

Into a 250 mL stainless steel autoclave, charged was 9.3 g (87.7 mmol) of dried $Na_2CO_3$. Then, the autoclave was cooled in dry ice/acetone, and 23.2 g (175.4 mmol) of $CF_3COCl$ was charged and reacted with stirring. A reaction temperature was from 21.4° C. to 31.7° C. and a reaction time was 80 minutes. A maximum pressure was 0.8 MPa. A yield was 89.7% according to $^{19}$F-NMR (Conversion: 89.7% and Selectivity: 100%).

EXAMPLE 2

Into 250 mL stainless steel autoclave, charged was 8.2 g (77.4 mmol) of dried $Na_2CO_3$. Then, 50 mL of $C_4F_6Cl_4$ as a solvent was charged. The autoclave was cooled in dry ice/acetone, and 21.7 g (163.8 mmol) of $CF_3COCl$ was charged and reacted with stirring. A reaction temperature was from 25.0° C. to 26.1° C. and a reaction time was 275 minutes. A maximum pressure was 0.37 MPa. A yield was 87.4% according to $^{19}$F-NMR (Conversion: 87.4% and Selectivity: 100%).

EXAMPLE 3

Into 250 mL stainless steel autoclave, charged was 9.3 g (87.7 mmol) of dried $Na_2CO_3$. Then, 50 mL of $C_4F_6Cl_4$ as a solvent was charged. Then, the autoclave was cooled in dry ice/acetone, and 25.2 g (190.2 mmol) of $CF_3COCl$ was charged and reacted with stirring. A reaction temperature was from 71.1° C. to 77.6° C. and a reaction time was 222 minutes. A maximum pressure was 0.83 MPa. A yield was 85.2% according to $^{19}$F-NMR (Conversion: 85.2% and Selectivity: 100%).

EXAMPLE 4

Into 250 mL stainless steel autoclave, charged was 9.4 g (88.7 mmol) of dried $Na_2CO_3$. Then, 50 mL of $C_6H_{14}$ as a solvent was charged. Then, the autoclave was cooled in dry ice/acetone, and 24.0 g (181.1 mmol) of $CF_3COCl$ was charged and reacted with stirring. A reaction temperature was from 22.1° C. to 25.0° C. and a reaction time was 231 minutes. A maximum pressure was 0.53 MPa. A yield was larger than 84.5% according to $^{19}$F-NMR (Conversion: >84.5% and Selectivity: 100%).

EXAMPLE 5

Into 250 mL stainless steel autoclave, charged was 9.6 g (90.6 mmol) of dried $Na_2CO_3$. Then, 50 mL of $CH_3CN$ as a solvent was charged. Then, the autoclave was cooled in dry ice/acetone, and 24.7 g (186.4 mmol) of $CF_3COCl$ was charged and reacted with stirring. A reaction temperature was from 21.6° C. to 60.0° C. and a reaction time was 175 minutes. A maximum pressure was 0.36 MPa. A yield was 74.0% according to $^{19}$F-NMR (Conversion: >74.0% and Selectivity: 100%).

EXAMPLE 6 (TWO-STEP REACTION)

Into a 500 mL stainless steel autoclave equipped with a fractionating column, charged were 200 g (1.89 mol) of $Na_2CO_3$ and 335 mL (260 g) of $CH_3CN$. Then, a system was replaced with vacuum, and the reaction was conducted in two steps.

In a first step, the autoclave was cooled in an ice bath, and each portion of $CF_3COCl$ (29 g) was charged and the charge was repeated (nine portions in total were charged) to conduct the reaction under the conditions of a charge time: 3 to 6 min., a reaction time after the charge: 10 min., and a $CO_2$ blow time after the reaction: 5 min. Total amount of $CF_3COCl$ used for the reaction was finally 254 g (1.92 mol). After the first step reaction, 300 mL of $CH_3CN$ was released at a reduced pressure of 400 mmHg.

After the release of $CH_3CN$, 259 g (1.96 mol) of $CF_3COCl$ was charged to conduct the second step reaction at a temperature of at most 40° C. A temperature at the completion of the reaction was 27° C. After the completion of the second step reaction, the distillation was conducted at a reduced pressure of 400 mmHg to recover 332 g (1.54 mol) of $(CF_3CO)_2O$. A yield was 81.6% according to $^{19}$F-NMR (Conversion: 81.6% and Selectivity: 100%).

EFFECT OF INVENTION

According to the present invention, $(R_fCO)_2O$ can be produced by using $R_fCOCl$ as a raw material in a one-step reaction.

What is claimed is:

1. A method of producing $(R_fCO)_2O$ by reacting $R_fCOCl$ with $M_mCO_3$, wherein $R_f$ is a saturated hydrocarbon group having 1 to 20 carbon atoms, which optionally has an oxygen atom, in which all or part of hydrogen atoms are substituted with a fluorine atom, or a fluorine atom and another halogen atom, M is an alkali metal or an alkali earth metal, m is 2 when M is the alkali metal, or 1 when M is the alkali earth metal.

2. The method according to claim 1, wherein a reaction temperature is from 0° C. to 150° C.

3. The method according to claim 1, wherein a reaction pressure is from atmospheric pressure to 2 MPa (gauge pressure).

4. The method according to claim 1, 2 or 3, wherein a polar solvent is used as a solvent.

5. The method according to claim 1, wherein the reaction is divided into two steps, and carbonate gas is drawn in a first step reaction.

6. The method according to claim 1, wherein produced $(RfCO_2)O$ is recovered by distillation under a reduced pressure.

* * * * *